(12) United States Patent
Wang et al.

(10) Patent No.: US 6,535,821 B2
(45) Date of Patent: Mar. 18, 2003

(54) SYSTEM AND METHOD OF BOLUS-CHASING ANGIOGRAPHY WITH ADAPTIVE REAL-TIME COMPUTED TOMOGRAPHY (CT)

(75) Inventors: Ge Wang, Iowa City, IA (US); Michael W. Vannier, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 58 days.

(21) Appl. No.: 09/781,919

(22) Filed: Feb. 9, 2001

(65) Prior Publication Data

US 2002/0010551 A1 Jan. 24, 2002

Related U.S. Application Data

(60) Provisional application No. 60/181,834, filed on Feb. 11, 2000.

(51) Int. Cl.$^7$ .............................. G01N 33/50; A61B 5/05
(52) U.S. Cl. ........................... 702/19; 702/84; 702/150; 600/415
(58) Field of Search ............................. 702/19, 20, 81, 702/84, 150, 182–183; 600/415–420; 324/306, 309

(56) References Cited

U.S. PATENT DOCUMENTS

| | | | |
|---|---|---|---|
| 5,713,358 A | * | 2/1998 | Mistretta et al. ............ 600/420 |
| 5,830,143 A | * | 11/1998 | Mistretta et al. ............ 600/420 |
| 6,230,040 B1 | * | 5/2001 | Wang et al. ................. 600/415 |

OTHER PUBLICATIONS

Jurriaans et al., "Bolus Chasing: A New Technique in Peripheral Arteriography," Clinical Radiology (1993) vol. 48, pp. 182–185.

Tublin et al., "Effect of Injection Rate of Contrast Medium on Pancreatic and Hepatic Helical CT," Radiology, (1999) vol. 210, pp. 97–101.

Katada, K., "Half–Second, Half–Millimeter Real–Time Multislice Helical CT: CT Diagnosis Using Aquillion™", Medical Review No. 68, pp. 31–38. (no date).

Watanabe, N., "Development of a Half–Second Real–Time Helical CT Scanner, Aquilion™", Medical Review No. 68, pp. 39–43. (no date).

Takase, K., "Helical CT with SureStart for the Examination of Patients with Vascular Disease," Medical Review No. 67, pp. 17–21. (no date).

Bae et al., "Aortic and Hepatic Peak Enhancement at CT: Effect of Contrast Medium Injection Rate—Pharmacokinetic Analysis and Experimental Pocine Model[1]," Radiology, 1998, vol. 206, pp. 455–464.

Bae et al., "Aortic and Hepatic Contrast Medium Enhancement at CT, Part I. Prediction with a Computer Model[1]," Radiology 1998, vol. 207, pp. 647–655.

(List continued on next page.)

*Primary Examiner*—Bryan Bui
(74) *Attorney, Agent, or Firm*—Needle & Rosenberg, PC

(57) ABSTRACT

The present invention is directed towards a system and method for optimization of contrast enhancement utilizing a bolus propagation model, a computerized predictor of the bolus position, and a real-time tomographic imaging system with an adaptive mechanism to move a patient and/or the imaging components. The system and method can be applied to X-ray CT angiography that relies on bolus peak prediction, real-time CT observation and adaptive table translation. In particular, the discrepancy between the bolus location predicted by a bolus propagation model and the real-time CT measurement is reconciled via a computerized predictor such as a linear extrpolator or a Kalman filter and fed into an adaptive table transport system to drive the table to chase the contrast bolus accordingly.

24 Claims, 9 Drawing Sheets

OTHER PUBLICATIONS

Bae et al., "Aortic and Hepatic Contrast Medium Enhancement at CT, Part II. Effect of Reduced Cardiac Output in a Porcine Model[1]", Radiology 1998, vol. 207, pp. 657–662.

Fleischmann et al., "Mathematical Analysis of Arterial Enhancement and Optimization of Bolus Geometry for CT Angiography Using the Discrete Fourier Transform," Journal of Computer Assisted Tomography, vol. 23, No. 3, 1999, pp. 474–484.

King et al., "Modeling in Physiology A Vascular Transport Operator," The American Physiological Society, 1993, Intravascular Transport, pp. H2196–H2208.

Wang et al., "Bolus–Chase MR Digital Subtraction Angiography in the Lower Extremity[1]," Radiology 1998, vol. 207, pp. 263–269.

Kopka et al., "Dual–Phase Helical CT of the Liver: Effects of Bolus Tracking and Different Volumes of Contrast Material[1]," Radiology, 1996, vol. 201, pp. 321–326.

Silverman et al., "Assessment of a Technology That Permits Individualized Scan Delays on Helical Hepatic CT: A Technique to Improve Efficiency in Use of Contrast Material," AJR, 1996, vol. 167, pp. 79–84.

Foley et al., "Technical Developments and Instrumentation, Digital Subtraction Angiography of the Extremities Using Table Translation[1]," Radiology, 1985; vol. 157, pp. 255–258.

Blomley et al., "Bolus Dynamics: Theoretical and Experimental Aspects," The British Journal of Radiology, Apr. 1997, pp. 351–359.

* cited by examiner (b) BLOCK DIAGRAM

SYSTEM AND METHOD OF BOLUS-CHASING ANGIOGRAPHY WITH ADAPTIVE REAL-TIME COMPUTED TOMOGRAPHY (CT)

CROSS-REFERENCE TO RELATED PATENT APPLICATION

This application claims the benefit, pursuant to 35 U.S.C. §120, of applicants' provisional U.S. Patent Application Serial No. 60/181,834, filed Feb. 11, 2000, entitled "BOLUS-CHASING ANGIOGRAPHY WITH ADAPTIVE REAL-TIME COMPUTED TOMOGRAPHY (CT)".

ACKNOWLEDGMENT

This invention was made partially with government support under NIDDK DK50184, DC03590, CA75371 and HD30169 awarded by the National Institutes of Health. The government has certain rights in the invention.

BACKGROUND OF THE INVENTION

1. Field of Invention

The present invention generally relates to a system and method for optimization of tomographic angiography utilizing a bolus propagation model, which can be applied to CT angiography that relies on bolus peak prediction, real-time CT observation and adaptive table transport.

2. Description of Prior Art

As known in the prior art, administration of a contrast material or bolus provides a short temporal window for optimally imaging the vasculature, lesions and tumors.

Optimization of contrast enhancement becomes increasingly crucial with the wide use of CT and Magnetic Resonant Image ("MRI") technology, given the dramatically shortened image acquisition time.

Recently, CT began a transition into sub-second scanning, cone-beam geometry and real-time imaging with the introduction of multi-slice systems.

A number of clinical studies were reported on contrast enhancement for CT over the past decade. However, the results on modeling of CT contrast bolus dynamics are limited to the compartmental model, which describes contrast enhancement specific to each entire compartment (organ or vessel).

To obtain the highest image quality in CT angiography at the lowest dosage of contrast material, strategies for bolus administration and CT data acquisition must be individualized and optimized. It is desirable to scan when the intravascular concentration of contrast material is at its peak.

Scanning too early may result in over-estimation of stenosis, while scanning too late may result in overlap of venous structures.

Three methods have been developed to individualize scan timing:

(1) test-bolus timing,
(2) region of interest (ROI) threshold triggering, and
(3) visual cue triggering.

For the test-bolus method, there is a risk of decreasing target lesion conspicuity due to equilibration of the test-bolus. For the two triggering methods, they are vulnerable to patient motion, usually related to breathing, which may displace the target organ or vessel from the scan plane.

Moreover, one of the fundamental limitations with all the three methods is that they provide little data for matching the table translation to the contrast bolus propagation. Bolus dynamics is complicated by multiple interacting factors involving the contrast administration protocol, imaging techniques, and patient characteristics. In particular, the current patient table is translated at a pre-specified speed during data acquisition, which cannot be altered adaptively to chase the contrast bolus for optimally enhanced CT images.

With a pre-set scanning speed, it is difficult and often impossible to synchronize the central scanning plane with the longitudinal bolus position. This mis-alignment becomes more problematic to image quality when spiral scanning speed is fast (with multi-slice spiral CT), contrast volume is small and/or injection rate is high (leading to reduced peak duration), as well as when there are large or small capacity vessels, either from aneurysm formation or occlusive disease.

Therefore, there is a need to develop a new system and method for synchronization of contrast administration and CT imaging that can maximize the signal differences between arteries and background and can be utilized to provide better tomographic angiography.

SUMMARY OF THE INVENTION

The present invention is directed towards a system and method for optimization of contrast enhancement utilizing a bolus propagation model, which can be applied to CT angiography that relies on bolus peak prediction, real-time CT observation and adaptive table transport. In particular, the discrepancy between the bolus location predicted by a bolus propagation model and the real-time CT observation is reconciled via a computerized predictor such as a linear extrapolator or a Kalman filter and fed into an adaptive table transport system to drive the table to chase the contrast bolus for optimally enhanced CT images.

In one embodiment of the present invention, a system of utilizing bolus propagation for contrast enhancement has a monitoring means for measuring the position of a bolus moving along a path in a biological structure, wherein the biological structure has a plurality of organs and vessels and is positioned on a table. The system also has a processing means for performing the steps of determining a predicted position of the bolus using a bolus propagation model with a set of parameters prior to the arrival of the bolus at a location of the path, and comparing the predicted position of the bolus with the measured position of the bolus. The system further has a filtering means for reconciling discrepancy, if any, between the predicted position of the bolus and the measured position of the bolus to extrapolate a set of control parameters, and a control means for receiving the set of control parameters to adaptively transport the table to chase the motion of the bolus. The filtering means includes a computerized predictor such as a linear extrapolator or a Kalman filter.

In another embodiment, the present invention relates to a system for utilizing bolus propagation for contrast enhancement. The system has an output device for injecting a bolus into a biological structure having a plurality of organs and vessels and being positioned on a table, a scanner for generating CT fluoroscopy image data of the bolus along a path in the biological structure, and a processor, which performs the steps of determining a predicted position of the bolus using a bolus propagation model with a set of parameters prior to the arrival of the bolus at a location of the path by performing the substeps of:

(1) Defining an extended vascular operator for one of the plurality of organs and vessels with three parameters T, D and L, where T is the time counting from the bolus injection, D is the dispersion and L is the length of the path;

(2) Selecting a plurality of locations $p_i$ along the path, i=0, 1, ..., N, N is an integer greater than one, where real-time measurements can be made on each location $p_i$ by the monitoring means;

(3) Selecting a time threshold value $\epsilon$ and a dispersion threshold value $\delta$;

(4) Defining a velocity variable $A_i$ and a relative dispersion variable $B_i$ for each of the plurality of locations $p_i$ along the path, where i=i+1;

(5) Setting $A_i=A_{i-1}$ and $B_i=B_{i-1}$, wherein $A_0=L/T$, and $B_0=D/T$;

(6) Predicting the peak arrival time $t(p_i)$ and the relative dispersion $B(p_i)$ of the bolus at the location $p_i$ according to the following:

$$t(p_i)=t(p_{i-1})+(p_i-p_{i-1})/A_i,$$

and $$B(p_i)=B_i;$$

(7) Measuring the peak arrival time $t'(p_i)$ and the relative dispersion $B'(p_i)$ of the bolus at the location $p_i$;

(8) If $|t'(p_i)-t(p_i)|>\epsilon$, updating the velocity variable $A_i$ according to the following formula:

$$A_i=(p_i-p_{i-1})/(t'_i-t'_{i-1});$$

(9) If $|B'(p_i)-B(p_i)|>\delta$, updating the relative dispersion $B(p_i)$ of the bolus according to the following formula:

$$B_i=B'(p_i);$$

(10) Updating T and D according to the following:

$$T=t_i+(L-p_i)/A_i;$$

and $$D=B_i;$$

and

(11) repeating steps (6)–(10) until all points of interest in the plurality of locations $p_i$ along the path have been selected;

and comparing the predicted position of the bolus with the image data of the bolus.

Moreover, the system includes a computerized predictor such as a linear extrapolator or a Kalman filter for reconciling discrepancy, if any, between the predicted position of the bolus and the image data of the bolus to extrapolate a set of control parameters, and a table transport system for adaptively transporting the table to chase the motion of the bolus to the set of control parameters.

In yet another embodiment, the present invention relates to a computer-readable, digital storage device storing executable instructions which cause a processor to utilize bolus propagation for CT angiography in a biological structure having a plurality of organs and vessels and being positioned on a table by:

(a) receiving image data associated with a bolus moving along a path in the biological structure;

(b) determining a predicted position of the bolus using a bolus propagation model with a set of parameters prior to the arrival of the bolus at a location of the path;

(c) comparing the predicted position of the bolus with the image data associated with the bolus;

(d) reconciling discrepancy, if any, between the predicted position of the bolus and the image data of the bolus to extrapolate a set of control parameters; and (e) feeding the set of control parameters to a control unit for adaptively transporting the table to chase the motion of the bolus accordingly.

In a further embodiment, the present invention relates to method for utilizing bolus propagation for CT angiography comprising the steps of:

(a) measuring the position of a bolus moving along a path in a biological structure, wherein the biological structure has a plurality of organs and vessels and is positioned on a table;

(b) determining a predicted position of the bolus using a bolus propagation model with a set of parameters prior to the arrival of the bolus at a location of the path;

(c) comparing the predicted position of the bolus with the traced position of the bolus to update the parameters;

(d) reconciling discrepancy, if any, between the predicted position of the bolus and the measured position of the bolus to extrapolate a set of control parameters; and (e) adaptively transporting the table to chase the motion of the bolus according to the set of control parameters.

DETAILED DESCRIPTION OF THE INVENTION

The present invention is more particularly described in the following examples that are intended as illustrative only since numerous modifications and variations therein will be apparent to those skilled in the art. As used in the specification and in the claims, "a" can mean one or more, depending upon the context in which it is used. The preferred embodiment is now described with reference to the Figures, in which like numbers indicate like parts throughout the Figures.

The present invention utilizes a bolus propagation model in terms of extended vascular operators. In one embodiment of the present invention, the bolus propagation model utilizes computation of the bolus concentration with respective to both the time counting from a bolus injection into a vessel and the location along the vessel, and can be applied to tomographic angiography and other applications.

Traditional Vascular Operator

It has been known as a workable approximation that a vascular transport path, either a large/small vessel or an organ, can be represented by a linear spatially invariant operator. In other words, the outflow concentration $C_{out}(t)$ may be expressed as convolution of the system point spread function H(t) and the inflow concentration $C_{in}(t)$:

$$C_{out}(t)=H(t) \otimes C_{in}(t). \quad (1)$$

Figure 1:
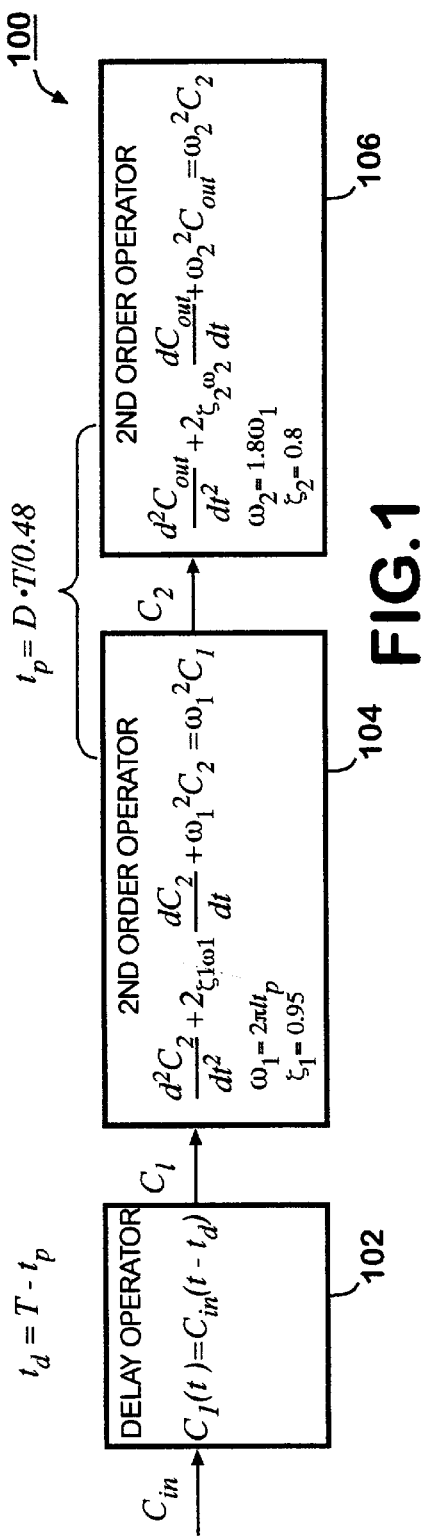
FIG. 1 illustrates a traditional vascular transport operator.

The vascular transport operator, $C_i(t)$, i=1, 2, . . . , is a parameterized form of H(t). As illustrated in FIG. 1, a traditional vascular transport operator consists of two components: a transmission line of delay $t_d$ and a dispersive unit of delay $t_p$ from a fourth-order Paynter operator with a fixed relative dispersion $D_p=0.48$. The delay operator 102 inputs $C_{in}(t)$, and gives $C_1(t)$. The Paynter operator takes $C_1(t)$, and outputs $C_{out}(t)$ as defined by the two second-order operators 104, 106:

$$d^2C_2(t)/dt^2+2\zeta_1\omega_1 dC_2(t)/dt+\omega_1^2=\omega_1^2 C_1(t), \quad (2)$$

and $$d^2C_{out}(t)/dt^2+2\zeta_2\omega_2 dC_{out}(t)/dt+\omega_2^2=\omega_2^2 C_2(t), \quad (3)$$

where $\omega_1$, $\omega_2$ being the natural frequency, $\zeta_1$, $\zeta_2$ being the damping factor. In one embodiment of the present invention, $\omega_1$, $\omega_2$, $\zeta_1$ and $\zeta_2$ are chosen as $\omega_1=2\pi/t_p$, $\zeta_1=0.95$, $\omega_2=1.82\ \omega_1$, and $\zeta_2=0.8$.

The vascular transport operator is characterized by the two delay parameters $t_d$ and $t_p$, or equivalently by the transit time T and the relative dispersion D. The transit time T through the path equals to the first moment of H(t). It can be shown that $$T=t_d+t_p. \quad (4)$$

The relative dispersion D is defined as:

$$D=\sigma/T, \quad (5)$$

where σ is the standard deviation of H(t). It can be proved that $$D=D_p t_p/T=(0.48\ t_p)/T. \quad (6)$$

Figure 1A:
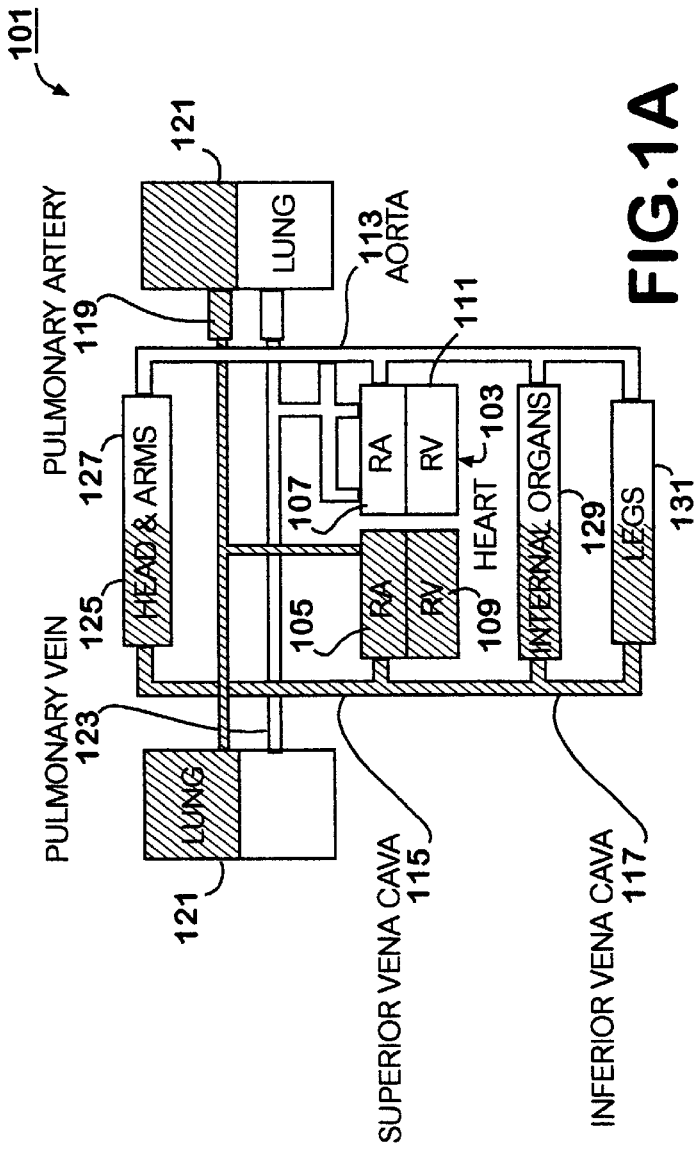
FIG. 1A illustrates a blood circulatory system of a patient that can be utilized in one embodiment of the present invention.

As illustrated in FIG. 1A, a blood circulatory system of a patient may be modeled as the system 101, where the heart 103 circulates blood in the body. The heart is divided into left and right halves. Each half has two chambers: an Atrium which receives blood, and a ventricle which sends blood. Thus, the system 103 has right atrium 105, left atrium 107, right ventricle 109, and left ventricle 111. Blood carrying waste from cells is pushed into the heart through large veins (Superior Vena Cava 115 and Inferior Vena Cava 117), then from the heart 103 through Pulmonary Arteries 119 into the lungs 121 for oxygen; and fed back through pulmonary Veins 123 to the heart 103. The heart 103 pumps the oxygen-rich blood into the main artery (Aorta) 113 and around the body head 125, arms 127, internal organs 129 and legs 131.

To utilize the circulatory system 101, one needs parameters for the circulatory system, typical values of which are given in Table I.

TABLE I

| Vessels | Diameter (mm) | Length (cm) | Thickness (mm) | Volume (cm³) | Pressure (mmHg) | Speed (cm/s) | Reynolds Number |
|---|---|---|---|---|---|---|---|
| Aorta | 25 | 40 | 2 | 100 | 100 | 40 | 3000 |
| Arteries | 0.15–15 | 15 | 0.8 | 350 | 90 | 10–40 | 500 |
| Veins | 0.15–15 | 18 | 0.6 | 2500 | 10–15 | 0.3–5 | 150 |
| Vena Cava | 30 | 40 | 1.5 | 300 | 5–10 | 5–30 | 3000 |

Extended Vascular Operator

Although there is no any physiological counterpart to each component of the vascular transport operator, their serial combination accurately describes the dispersion of intravenous bolus through a blood flow path, which is regarded as a black box.

Figure 2:
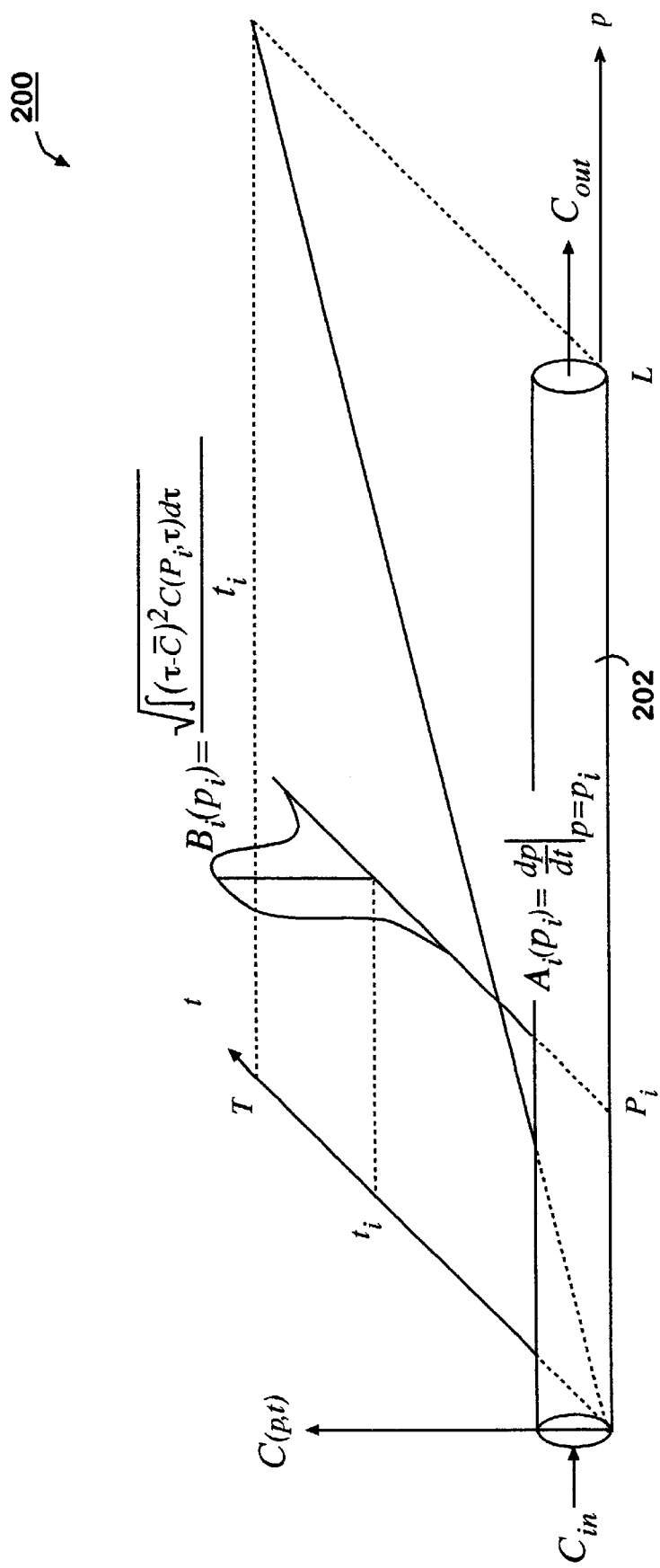
FIG. 2 illustrates an extended vascular transport operator with an additional parameter: vessel length L, according to one embodiment of the present invention.

To predict the bolus concentration as a function of the longitudinal location p along a vessel 202 and the time T since the bolus injection, according to one embodiment of the present invention, as shown in FIG. 2, a traditional vascular transport operator is extended to include the vessel length L as an additional parameter to produce an extended vascular transport operator C(p, t) 200 representing the bolus concentration. Furthermore, the present invention assumes that both of the bolus speed and the change rate of the standard deviation of H(t) are uniform or substantially uniform.

Under this assumption, the extended vascular operator C(p, t) can be expressed as follows:

$$C(p,\ t)=h(p,\ t) \otimes C_{in}(t), \quad (7)$$

where $$h(p,\ t)=(L/p)H((L/p)t), \quad (8)$$

$$H(t)=f_0(t) \otimes f_1(t) \otimes f_2(t), \quad (9)$$

$$f_0(t)=\delta(t-t_d), \quad (10)$$

$$f_1(t)=\exp(-\zeta_1\omega_1 t)\cos(\omega_1(1-\zeta_1^2 t)^{1/2}+\theta_1)u(t)/(1-\zeta_1^2)^{1/2}, \quad (11)$$

$$\theta_1=-\cos^{-1}((1-\zeta_1^2)^{1/2})-\pi,$$

$$f_2(t)=\exp(-\zeta_2\omega_2 t)\cos(\omega_2(1-\zeta_2^2 t)^{1/2}+\theta_2)u(t)/(1-\zeta_2^2)^{1/2}, \quad (12)$$

and $$\theta_2=-\cos^{-1}((1-\zeta_2^2)^{1/2})-\pi.$$

Substituting the fixed parameters, $\omega_1$, $\omega_2$, $\zeta_1$ and $\zeta_2$, as given above, into (11)

Equations (11) and (12), one can have:

$$f_1(t)\approx 3.20\ \exp(-5.97\ t/t_p)\cos(\omega_1(1.96\ t/t_p-4.39))(u(t), \quad (13)$$

$$f_2(t)\approx 1.67\ \exp(-9.15\ t/t_p)\cos(\omega_1(6.86\ t/t_p-4.07))(u(t). \quad (14)$$

It can be further verified that $$\lim_{p \to 0} h(p, t) = \delta(t), \quad (15)$$

and $$\lim_{p \to L} h(p, t) = H(t). \quad (16)$$

Parameter Adjustment Algorithm

Figure 3:
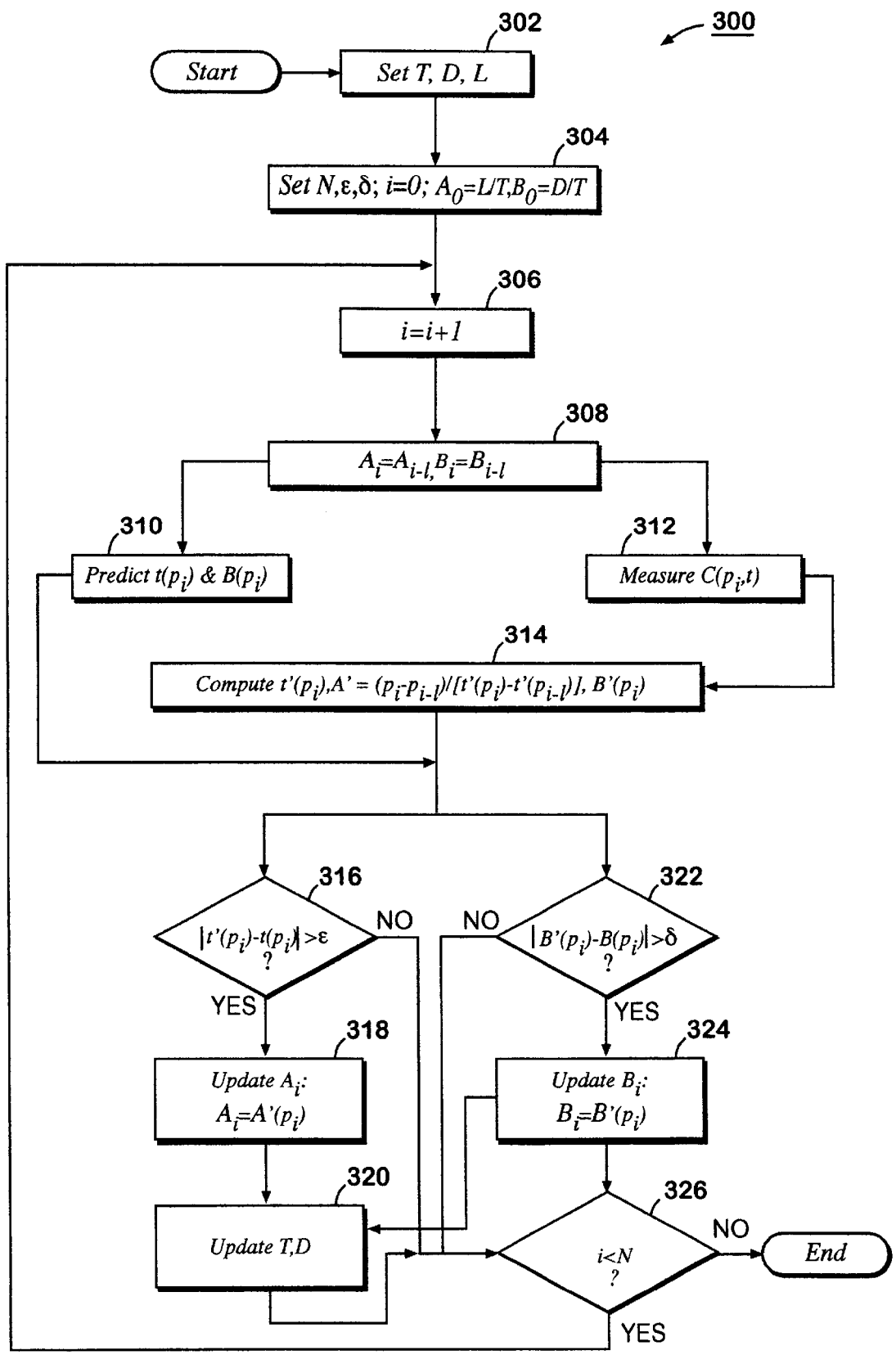
FIG. 3 is a flow chart of a parameter adjustment algorithm according one embodiment of the present invention.

Referring now to FIGS. 2 and 3, the bolus concentration can be predicted by the extended vascular operator C(p, t) defined above, and can also be measured by CTF performed at multiple locations, $p_i$ along the vessel 202, i=0, 1, . . . , N, N is an integer greater than one. The vessel 202 can represent an organ, a vessel, or a combination. To compensate for possible discrepancies between the bolus concentration predicted by the extended vascular operator C(p, t) and the real bolus propagation measured by CTF, a parameter adjustment algorithm is developed according to one embodiment of the present invention.

Referring now to FIG. 3, in one aspect of the present invention, a parameter adjustment algorithm 300 for compensating for possible discrepancies between the bolus concentration predicted by the extended vascular operator C(p, t) and the real bolus propagation measured by CTF is described in more details.

At step 302, an extended vascular operator for one of the plurality of organs and vessels with three parameters T, D and L is defined, where T is the time counting from the bolus injection, D is the dispersion and L is the length of the vessel 202, or a path. At step 304, a plurality of locations $p_i$ along the vessel 202 is selected, where i=0, 1, . . . , N, N is an integer greater than one, and real-time measurements can be made on each location $p_i$ by a monitoring means such as CTF. Additionally, a time threshold value $\epsilon$ and a dispersion threshold value $\delta$ are selected.

At step 306, index i is reset as i=i+1. At step 308, a velocity variable $A_i$ and a relative dispersion variable $B_i$ for each of the plurality of locations $p_i$ along the vessel is set with $A_i = A_{i-1}$ and $B_i = B_{i-1}$, wherein $A_0 = L/T$, and $B_0 = D/T$. At step 310, the peak arrival time $t(p_i)$ and the relative dispersion $B(p_i)$ of the bolus at the location $p_i$ according to the following:

$$t(p_i) = t(p_{i-1}) + (p_i - p_{i-1})/A_i,$$

and $$B(p_i) = B_i.$$

At steps 312–314, the peak arrival time $t'(p_i)$ and the relative dispersion $B'(p_i)$ of the bolus at the location $p_i$ are measured. At step 316, check if $|t'(p_i) - t(p_i)| > \epsilon$. If yes, at step 318, update the velocity variable $A_i$ according to the following formula:

$$A_i = (p_i - p_{i-1})/(t'_i - t'_{i-1}),$$

if not, go to step 326 for next point of interest. At step 322, check if $|B'(p_i) - B(p_i)| > \delta$. If yes, at step 324, update the relative dispersion $B(p_i)$ of the bolus according to the following formula:

$$B_i = B'(p_i),$$

if not, go to step 326 for next point of interest. At step 320, update T and D according to the following:

$$T = t_i + (L - p_i)/A_i;$$

and $$D = B_i,$$

and then go to step 326 for next point of interest. Steps (306)–(326) are repeated until all points of interest in the plurality of locations $p_i$ along the vessel 202 have been selected.

Note that the dynamic adjustment to the bolus speed and the relative dispersion given here is based on a piece-wise constant assumption as a way of example, not a way of limitation. Higher-order adjustment can be similarly embedded into the algorithm illustrated in FIG. 3. By adaptively changing the parameters of the vascular operator, modeling errors would be promptly corrected.

Bolus Propagation Model

As discussed above, an extended vascular operator C(p, t) can be utilized to represent a vascular transport path including a vessel, an organ, or a combination of them. In a complicated biological structure such as a human body, a plurality of vessels, organs, and combinations of them exist. To synchronize the aperture of the X-ray beam and the passage of the bolus peak for optimal CT angiography in such a complicated biological structure, in another aspect of the present invention, a bolus propagation model in terms of extended vascular operators is developed and illustrated in FIG. 4.

Figure 4:
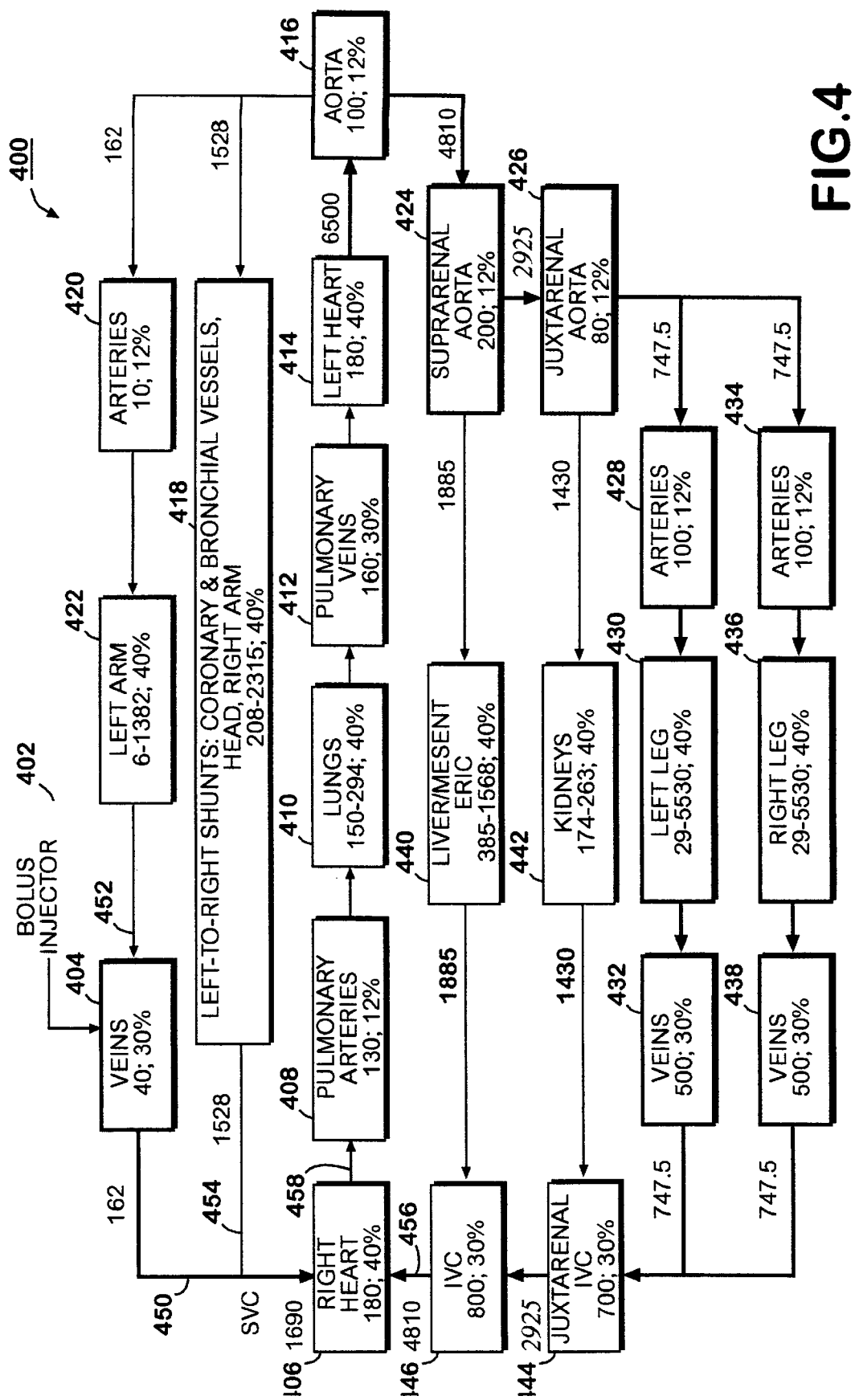
FIG. 4 depicts a biological system in term of the bolus propagation model according to one embodiment of the present invention.

As shown in FIG. 4, a biological system 400 such as a human being has organs and vessels, or components in term of the bolus propagation model according to one embodiment of the present invention. The components may include head, heart, lungs, superior vena cava, inferior vena cava, aorta, as well as arteries and veins in arms, thorax, abdomen, pelvis, and legs, etc. Every component is treated as a linear spatially invariant system, and may be partitioned into linear sub-systems. Each system or sub-system is then transformed to an extended vascular transport operator, which has three parameters and can be dynamically adjusted using the algorithm described above. As shown in FIG. 4, the biological system 400 allows a bolus injector 402 to inject a bolus into the biological system 400 through veins 404. The biological system 400 also has right heart 406, pulmonary arteries 408, lungs 410, pulmonary veins 412, left heart 414, aorta 416, suprarenal aorta 424, juxtarenal aorta 426, arteries 428, 434, left and right legs 430, 436, veins 432, 438, liver/mesenteric 440, kidneys 442, juxtarental IVC 444, IVC 446, left-to-right shunts: corronary and bronchial vessels, head, and right arm 418, arteries 420, and left arm 422. The biological system 400 may include other organs or components. All these organs and vessels, or components are coupled to each other, one way or another, in the biological system 400.

One advantage of the biological system 400 is to allow a quantitative description of the longitudinal and temporal distribution of the contrast material concentration. As shown in FIG. 4, an organ, a vessel, or a combination is represented in a box. For examples, box 406 represents right heart (an organ) while box 404 represents veins coupled to right heart 406. A box is treated as a linear system and may be partitioned into sub-systems. Each system or sub-system can be characterized by an extended vascular transport operator as defined above. Each box is connected to at least one neighboring box by a vector, which denotes the blood flow. For example, box 404 representing veins is connected to neighboring box 406 representing right heart 406 by vector 450. The direction of the vector 450 indicates that the flow of blood is from box 404 to box 406. Box 404 is also connected to neighboring box 422 representing left arm by vector 452. The direction of the vector 452 indicates that the flow of blood is from box 422 to box 404.

Moreover, the values of intravascular and extracellular volumes, as well as relative dispersion, can be derived from the literature. The parameters of an extended vascular operator for an organ, a vessel, or a combination should be individualized in clinical applications. It was reported that blood volume V (in milliliters) and cardiac output O (in milliliters per minute) can be predicted in terms of gender, weight W (in pounds) and height H (in inches). For a man of 100–310 lb (or 45–140 kg) and 60–74 inches (or 152–188 cm), $V=33.165H^{0.725}W^{0.425}-1229$. For a woman of 80–290 lb (or 36–130 kg) and 60–74 inches (152–188 cm), $V=34.85^{0.725} W^{0.425}-1954$. For a woman or a man, $O=36.36^{0.725} W^{0.425}$. The predicted values of V and O are then used to proportionally adjust the values of the volumes and the flows for each component in the biological system 400 as shown in FIG. 4.

For boxes corresponding to vessels, the first number represents the intravascular volume (in milliliters) and the second number represents the relative dispersion (as a percentage). For examples, for box 404 representing veins, the first number "40" indicates the intravascular volume of veins as 40 milliliters, and the second number "30%" indicates the relative dispersion as 30%.

For boxes corresponding to organs, the first two numbers represent the intravascular and extracellular volumes (in milliliters), respectively, and the third number represents the relative dispersion (as a percentage). For examples, for box 422 representing left arm, the first two numbers "6-1382" represent the intravascular volume of the left arm as 6 milliliters and extracellular volume of the left arm as 1,382 milliliters, respectively, and the third number "40%" indicates the relative dispersion as 40%.

Additionally, data are given for vectors connecting boxes representing the flow of blood between boxes in the form of a number near a vector in the unit of milliliters per minute. For example, for vector 456 connecting box 446 representing IVC and box 406 representing right heart, the number 4810 near the vector 456 indicates that the flow of blood from box 446 to box 406 is 4,810 milliliters per minute. Note that for a given box, the incoming flow of blood to the box equals to the outputting flow of blood from the box. For example, for box 446, the sum of the incoming flow of blood from box 444, 2,925 milliliters per minute, and the incoming flow of blood from box 440, 1,885 milliliters per minute, equals to the outputting flow of blood from box 446 to box 406, 4,810 milliliters per minute.

As far as the length values of the extended vascular operators are concerned, the representative data can be obtained from an average, visible man and woman (http://www.nlm.nih.gov/research/visible/visible/_human.html) then proportionally modified according to the height of an individual patient at issue. The transit time can be computed as either the volume over the flow or the length over the speed. The speed may be directly measured using MRI or ultrasound. The relative dispersion values are set based on previous measurements for arteries (121%), veins (30%), and whole organs (40%). Also, the parameters of the extended vascular operator can be identified using the test-bolus approach.

APPLICATIONS OF THE PRESENT INVENTION

The following provide details for several applications of the present invention.

In one aspect, the present invention can be utilized in design of the bolus geometry. It is known in the art that the bolus geometry determines the concentration-time curves of the vasculature. Insufficient arterial opacification may result in nondiagnostic image quality, and excessive opacification may lead to artifacts. Thus, one objective of the bolus geometry design is to specify the bolus profile at an injection site so that a pre-defined arterial opacification level can be achieved at target segment(s) as uniformly as possible for the entire scanning period.

Recently, a clinically applicable algorithm was developed to analyze and optimize individual arterial enhancement in CTA. Assuming a time-invariant linear system, the discrete Fourier transform was used to calculate the transfer function of the system, which is called the "patient function", from the arterial response to a test bolus. The patient function was subsequently used to predict aortic enhancement and optimize biphasic injection protocols in patients undergoing CTA of the abdominal aorta.

In one embodiment of the present invention, the patient function can be computed from an individualized bolus propagation model as described above, instead of data from a test-bolus experiment. Subsequently, the input profile of the contrast bolus at an injection site was synthesized to give a desired contrast enhancement characteristics.

Figure 5A:
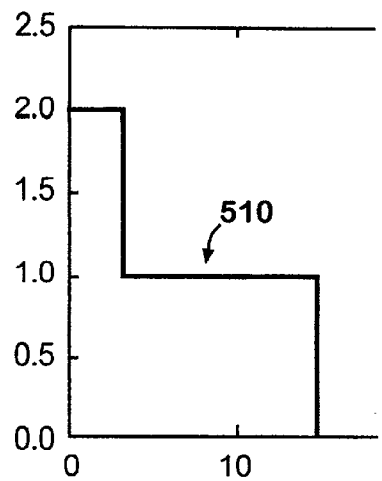
FIG. 5 depicts a representative case for using the bolus propagation model in design of the bolus geometry according to one embodiment of the present invention.
Figure 5B:
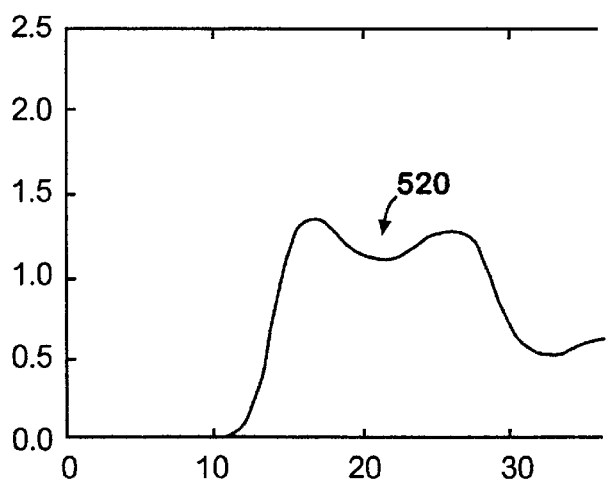
Figure 5C:
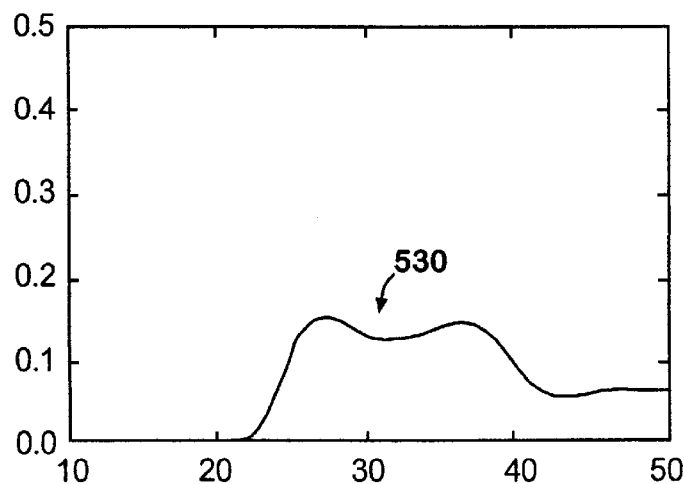

A representative case is presented in FIG. 5. In this case, a contrast bolus was injected at the middle of the left arm vein (not shown), then the CTA observation from the aortic arch to the runoff into the feet was made. In FIG. 5(a), a step-like curve 510 gives the input profile of the contrast bolus. In FIG. 5(b), curve 520 shows preferred plateaus of contrast enhancement at the aorta aortic arch. And in FIG. 5(c), curve 530 shows preferred plateaus of contrast enhancement at the middle of the left leg arteries.

In another aspect, the present invention can be utilized in assessment of the bolus dynamic propagation. An important determinant of bolus propagation is the cardiac function and the presence of central venous occlusion. Other factors such as IV site and body habitus are largely predictable before scanning. Bolus transit time from the peripheral IV to the right atrium is usually independent of cardiac function (except in severe tricuspid regurgitation and right-sided heart failure). The cardiac pump function governs bolus transit from the right atrium to the ascending aorta. The cardiac pump function is affected by the presence of cardiomyopathy (either right or left ventricular dysfunction, pericardial effusion, etc.), pulmonary hypertension, and valvular heart disease, hyperdymaic states.

Figure 6A:
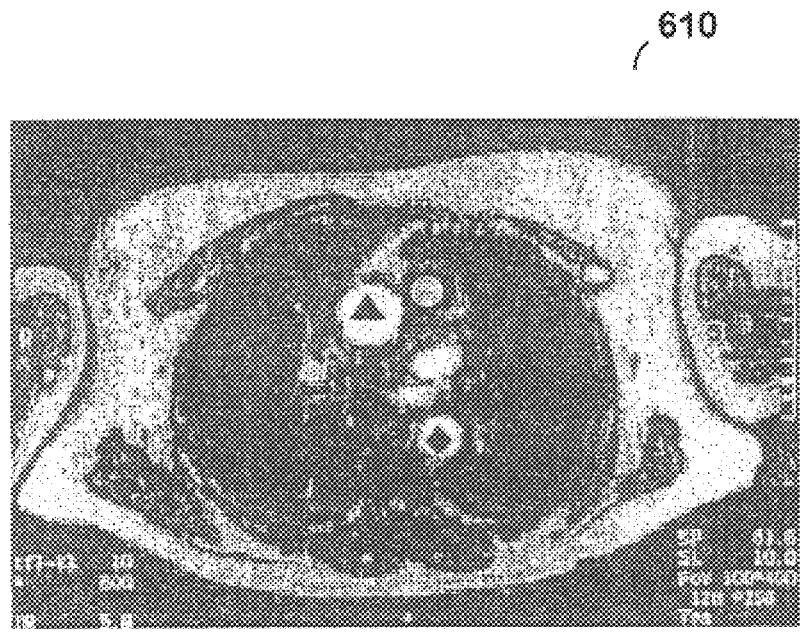
FIG. 6 depicts a representative patient study for bolus arrival delay assessment according to one embodiment of the present invention.
Figure 6B:
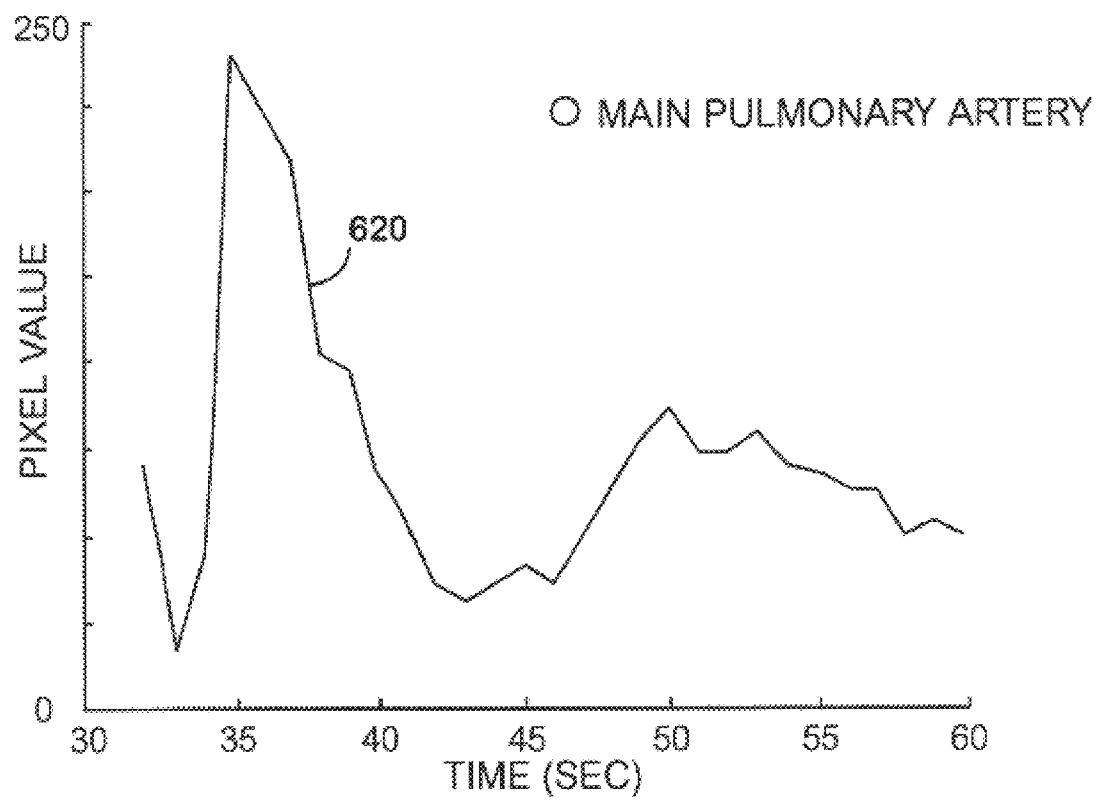
Figure 6C:
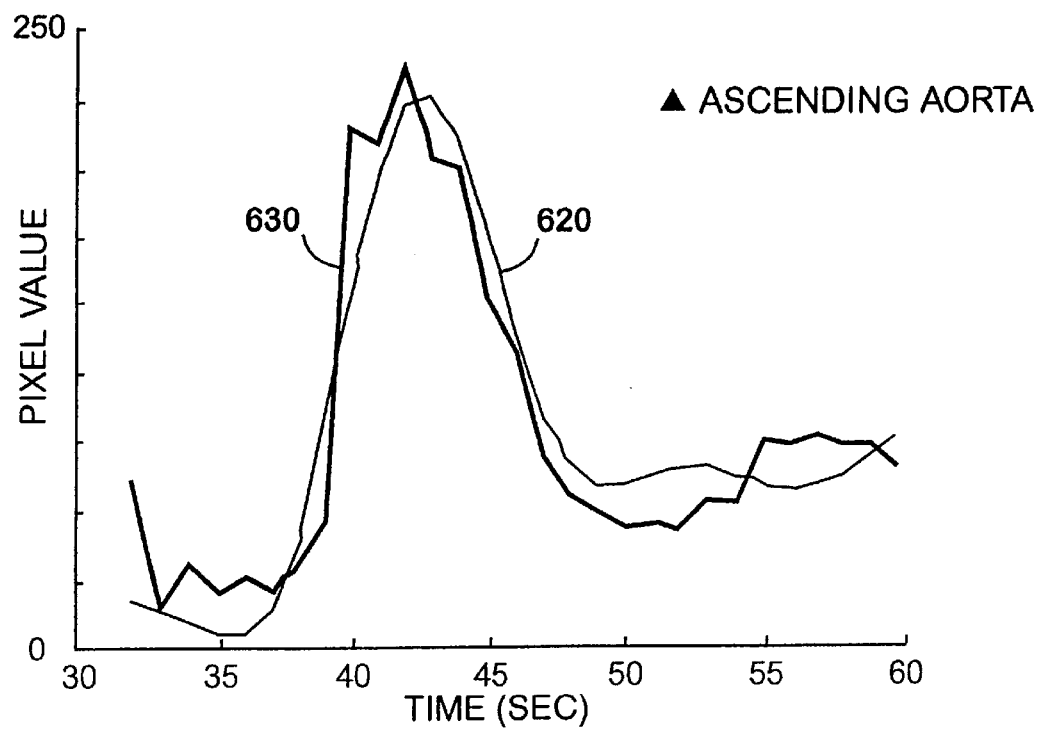
Figure 6D:
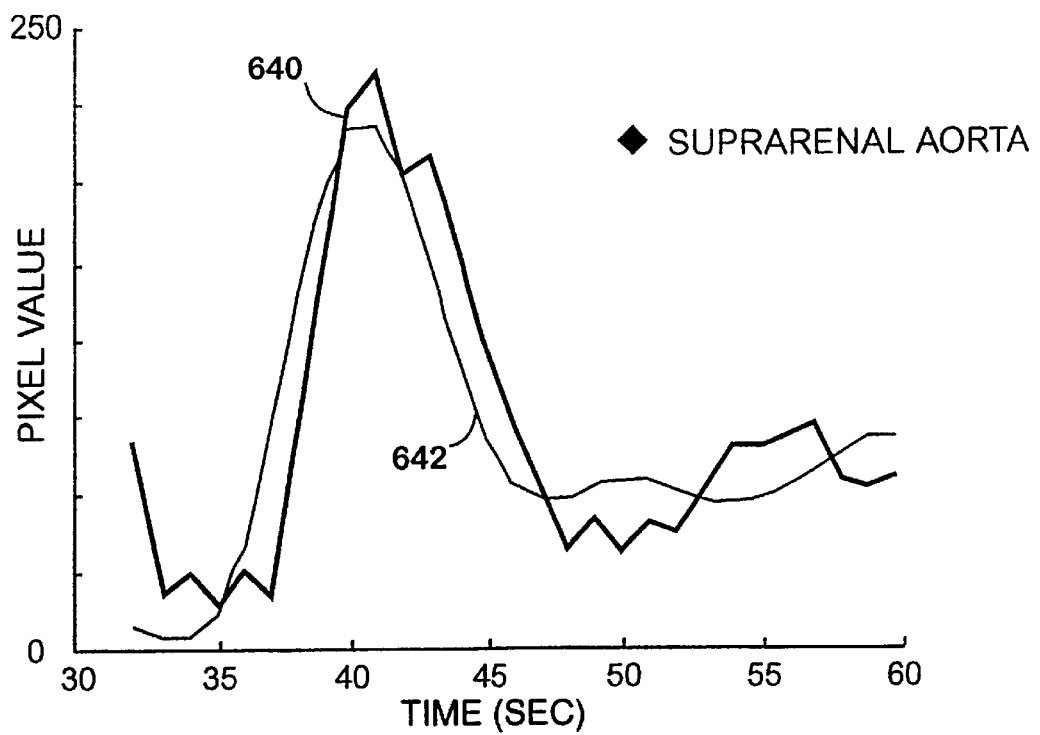

Using contrast enhanced axial MRI (turbo-FLASH sequence, TR: 5.8 msec, TE: 2.4 msec, flip angle: 10°, slice thickness: 10 mm, acquisition/sec), one can assess the flow characteristics in the cardiopulmonary circulation, evaluate the utility of the bolus propagation model and refine the model parameters. FIG. 6 illustrates a representative patient study. FIG. 6(a) shows a typical MR cardiac image 610 from a patient. FIGS. 6(b)–(d) show bolus arrival delays at three serial anatomic points. In FIG. 6(b), bolus arrival delay at the main pulmonary artery is shown, where curve 620 is an intensity-time curve generated from three regions of interest and acquired by performing a fast MRI in the axial plane at the rate of 1 acquisition/second. In FIG. 6(c), bolus arrival delay at the ascending aorta is shown, where curve 630 is an intensity-time curve generated from three regions of interest and acquired by performing a fast MRI in the axial plane at the rate of 1 acquisition/second, and curve 632 is an intensity-time curve calculated from the bolus propagation model according to the present invention. In FIG. 6(d), bolus arrival delay at the suprarenal aorta is shown, where curve 640 is an intensity-time curve generated from three regions of interest and acquired by performing a fast MRI in the axial plane at the rate of 1 acquisition/second, and curve 642 is an intensity-time curve calculated from the bolus propagation model according to the present invention. One conclusion drawn from FIGS. 6(*a*)–(*d*) is that measured intensity-time curves and calculated from the bolus propagation model are in excellent agreement. Similarly, patient data using MRI, X-ray CT and DSA may also be utilized with the bolus propagation model to assess bolus propagation.

Figure 7:
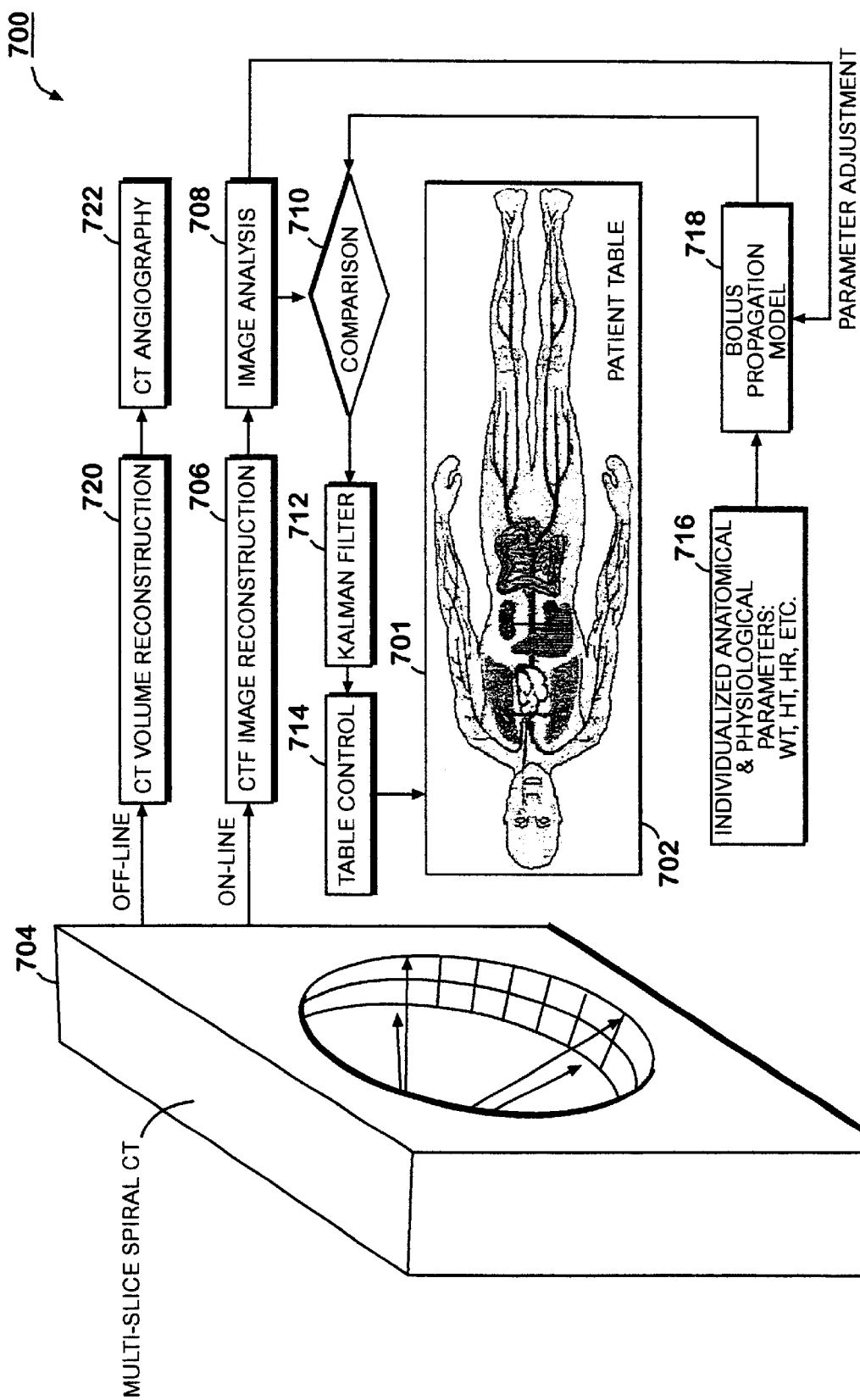
FIG. 7 depicts a process of utilizing bolus propagation for adaptive CT angiography according to one embodiment of the present invention.

In yet another aspect, the present invention can be utilized to provide an adaptive CT angiography. FIG. 7 shows a process 700 of utilizing bolus propagation for adaptive CT angiography according to one embodiment of the present invention. Currently, when a CT angiography is performed on a patient 701, the patient is positioned in a patient table 702. A bolus (not shown) is introduced into the patient 701 and can be monitored by CT fluoroscopy ("CTF"). The CTF can be performed on a spiral CT scanner 704 in single-slice, multi-slice or cone-beam configurations, in which case the patient 701 is scanned by the scanner 704. The issue is how to better monitor or chase the dynamic propagation of the bolus inside the body of the patient 701.

The bolus-chasing problem is akin to that of tracking an airplane by radar, where prediction of the target location is required to minimize the delay in positioning the antenna. A massive radar antenna cannot be moved to track such targets without prediction, based on a Kalman filter, of where the target will be at a time equal or greater to the antenna positioning delay. The analogy to predicting bolus arrival in the body and adjust table motion is striking and powerful.

Thus, the present invention utilizes the analogy and the bolus propagation model to predict the bolus location before its arrival, and translate the table 702 accordingly to capture the optimal image data. A computerized predictor such as a time-varying adaptive iterative Kalman filter 712 allows us to continually improve the quality of the prediction based on recently collected observations. Therefore, the present invention has a significant potential to improve tomographic angiography.

This approach is illustrated graphically in FIG. 7. Initially, a patient 701 is positioned at the patient table 702 and a bolus is injected into the patient 701 to move along a path in the blood circulatory system of the patient. At step 702, bolus position is monitored by CTF performed on the spiral CT scanner 704. At step 706, on-line image reconstruction is performed. At step 708, real-time image analysis is performed to produce images for the measured bolus position. In parallel, at step 716, a set of individualized anatomical and physiological parameters are provided. At step 718, a predicted position of the bolus using a bolus propagation model with the set of parameters prior to the arrival of the bolus at a location is calculated. The calculation can be made by using an extended vascular operator theory as discussed above or an alternative bolus propagation theory. At step 710, the predicted position of the bolus from step 718 and the measured bolus position are compared. At step 712, discrepancy, if any, between the predicted position of the bolus and the measured bolus position from step 710, is reconciled by a computerized predictor such as a Kalman filter or a linear extrapolator to extrapolate a set of control parameters. At step 714, the set of control parameters from step 710 is fed into a table control unit for adaptive table transport to chase the motion of the bolus. Consequently, synchronization of the bolus peak and the imaging aperture may be achieved dynamically by minimizing the discrepancies, if any, between the predicted and measured positions. Note that this process is dynamic and can be repeated until part or all points of the interest along the path in the blood circulatory system of the patient have been selected. Moreover, parameters used in the bolus propagation model at step 718 can be adjusted during the process by information gained from images for the measured bolus position at step 708. At step 720, after the CTF is performed or the scan is done on the patient 701, the off-line CT volume reconstruction is performed. At step 722, CT angiography is conducted.

Figure 8:
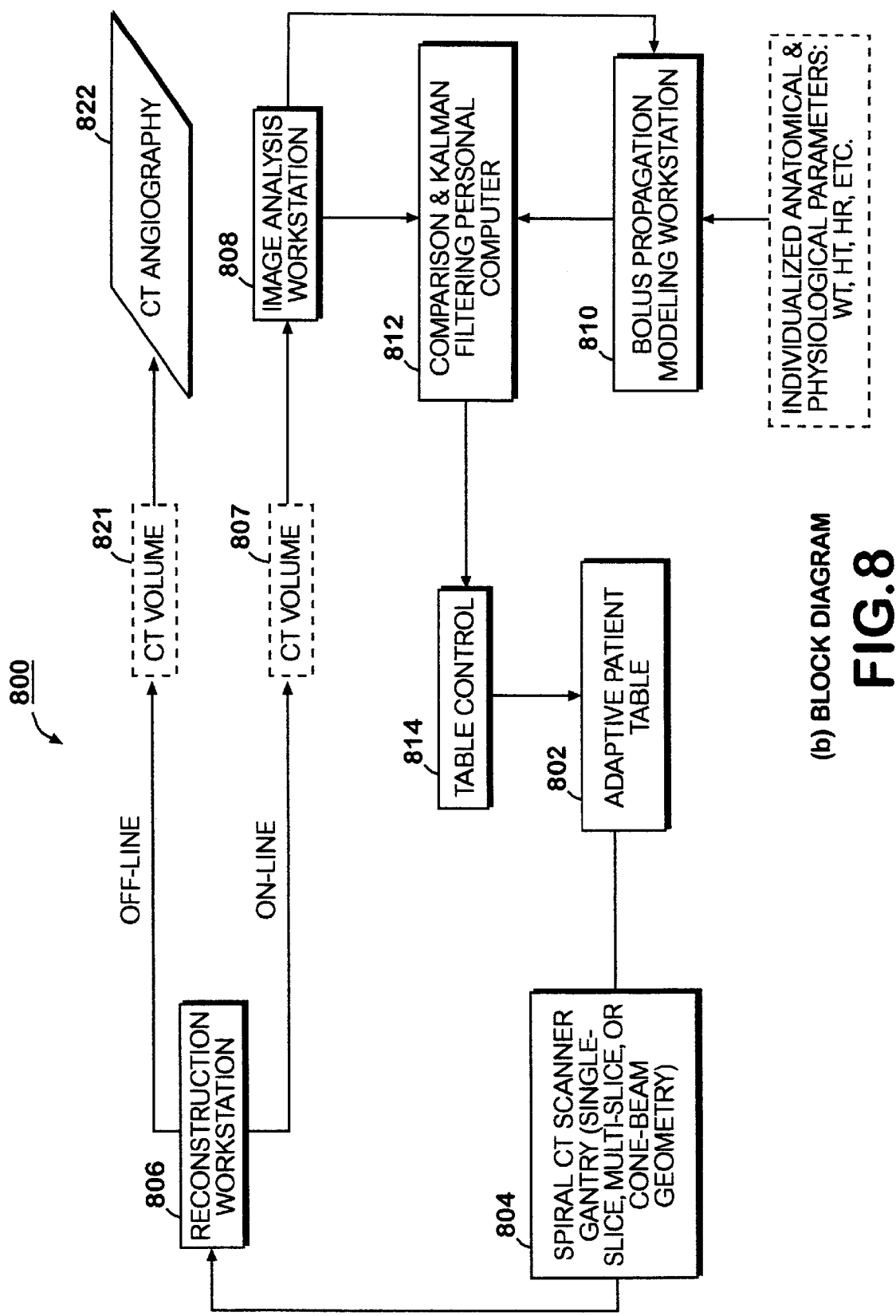
FIG. 8 shows a system for performing the process shown in FIG. 7 according to one embodiment of the present invention.

The process 700 according to the present invention can be performed by an adaptive CT angiography system which can have hardware and software. One such system 800 according to one embodiment of the present invention is shown in FIG. 8. The system 800 includes a patient table 802 for supporting a patient (not shown). The patient table 802 is adaptive to table control 814. The system 800 has a monitoring device 804 such as a spiral CT scanner to monitor the patient on the patient table 802, in particular, to monitor the propagation of a bolus (not shown) that is injected into the patient. Scanning can be performed in single slice, multi-slice, or cone-beam geometry. The system 800 also has a reconstruction workstation 806 coupled to the monitoring device 804, a workstation 808 coupled to the reconstruction workstation 806, a personal computer ("PC") 812 coupled to the workstation 808, and a workstation 810 coupled to PC 812, where the workstations 808 and 810 can also communicate to each other. The workstation 806 can perform on-line CTF image construction, as described above for step 706, and provide CTF images to the workstation 808 to conduct image analysis, as described above for step 708. The workstation 808 performs image analysis and outputs the results to PC 812, and to workstation 810 for adjusting parameters to be used in the bolus propagation model. The workstation 810 receives a set of parameters such as individualized anatomical and physiological parameters and calculates a predicted position of the bolus using a bolus propagation model with the set of parameters prior to the arrival of the bolus at a location. The parameters utilized in the bolus propagation model can be adjusted by the workstation 810 using the results of image analysis from the workstation 808. PC 812 reconciles discrepancy, if any, between the predicted position of the bolus and the measured bolus position by utilizing a computerized predictor such as a Kalman filter or a linear extrapolator to extrapolate a set of control parameters, which are received in the table control 814 to drive the patient table 802 accordingly. The workstation 806 also performs off-line CT volume reconstruction to provide CT volume 821 for CT angiography 822.

While the system 800 as shown in FIG. 8 has a plurality of workstations or computers, it can have more or less workstations. Indeed, the functions performed by workstation 806, workstation 808, PC 812, and workstation 810 can be performed by just one workstation or computer having a processor that has proper memory, speed and power. Moreover, even if more than one workstations or computers are utilized, a different configuration than the one given in FIG. 8 may be used to practice the present invention.

As those skilled in the art will appreciate, the mechanism of the present invention is capable of being distributed in the form of a computer readable medium of instructions in a variety of forms, and the present invention applies equally regardless of the particular type of signal bearing media used to actually carry out the distribution. Examples of computer readable media include: recordable type media such as floppy disks and CD-ROMs and transmission type media such as digital and analog communication links.

Although the present invention has been described with reference to certain preferred embodiments thereof, variations and modification of the present invention can be effected within the spirit and scope of the following claims. For example, while the present invention is described with respect to CT angiography, it can be readily utilized in radiographic angiography, MRI, or other medical applications using contrast enhancement.

What is claimed is:

1. A system of utilizing bolus propagation for contrast enhancement comprising:
   (a) a monitoring means for measuring the position of a bolus moving along a path in a biological structure, wherein the biological structure has a plurality of organs and vessels and is positioned on a table;
   (b) a processing means for performing the steps of:
      (i) determining a predicted position of the bolus using a bolus propagation model with a set of parameters prior to the arrival of the bolus at a location of the path; and
      (ii) comparing the predicted position of the bolus with the measured position of the bolus;
   (c) a filtering means for reconciling discrepancy, if any, between the predicted position of the bolus and the measured position of the bolus to extrapolate a set of control parameters; and
   (d) a control means for receiving the set of control parameters to adaptively transport the table to chase the motion of the bolus.

2. The system of claim 1, wherein the predicted position of the bolus is determined by performing the substeps of:
   (1) Defining an extended vascular operator for each of the plurality of organs and vessels with three parameters T, D and L, where T is the time counting from the bolus injection, D is the dispersion and L is the length of the path;
   (2) Selecting a plurality of locations $p_i$ along the path, i=0, 1, . . . , N, N is an integer greater than one, where real-time measurements can be made on each location $p_i$ by the monitoring means;
   (3) Selecting a time threshold value $\epsilon$ and a dispersion threshold value $\delta$;
   (4) Defining a velocity variable $A_i$ and a relative dispersion variable $B_i$ for each of the plurality of locations $p_i$ along the path, where i=i+1;
   (5) Setting $A_i=A_{i-1}$ and $B_i=B_{i-1}$, wherein $A_0=L/T$, and $B_0=D/T$;
   (6) Predicting the peak arrival time $t(p_i)$ and the relative dispersion $B(p_i)$ of the bolus at the location $p_i$ according to the following:

$t(p_i)=t(p_{i-1})+(p_i-p_{i-1})/A_i$, and $B(p_i)=B_i$;

(7) Measuring the peak arrival time $t'(p_1)$ and the relative dispersion $B'(p_i)$ of the bolus at the location $p_i$;
   (8) If $|t'(p_i)-t(p_i)|>\epsilon$, updating the velocity variable $A_i$ according to the following formula:

$A_i=(p_i-p_{i-1})/(t'_i-t'_{i-1})$;

(9) If $|B'(p_i)-B(p_i)|>\delta$, updating the relative dispersion $B(p_i)$ of the bolus according to the following formula:

$B_i=B'(p_i)$;

(10) Updating T and D according to the following:

$T=t_i+(L-p_i)/A_i$;

and $D=B_i$;

and

(11) repeating steps (6)–(10) until all points of interest in the plurality of locations $p_i$ along the path have been selected.

3. The system of claim 2, wherein the extended vascular operator represents the bolus concentration as a function of the variables t, p and L, wherein t=T and p is the point of interest at time t.

4. The system of claim 3, wherein the extended vascular operator takes the following form:

$C(p, t)=h(p, t) \otimes C_{in}(t)$, where $C(p, t)$ is the extended vascular operator, $h(p, t)=(L/p)H((L/p)t)$, $H(t)=f_0(t) \otimes f_1(t) \otimes f_2(t)$, $f_0(t)=\delta(t-t_d)$, $f_1(t)=\exp(-\zeta_1\omega_1 t)\cos(\omega_1(1-\zeta_1^2 t)^{1/2}+\theta_1)u(t)/(1-\zeta_1^2)^{1/2}$, $\theta_1=-\cos^{-1}((1-\zeta_1^2)^{1/2})-\pi$, $f_2(t)=\exp(-\zeta_2\omega_2 t)\cos(\omega_2(1-\zeta_2^2 t)^{1/2}+\theta_2)u(t)/(1-\zeta_2^2)^{1/2}$, and $\theta_2=-\cos^{-1}((1-\zeta_2^2)^{1/2})-\pi$, with $\omega_1$, $\omega_2$ being the natural frequency, $\zeta_1$, $\zeta_2$ being the damping factor, and $t_d$ representing a transmission line of delay.

5. The system of claim 4, wherein $\omega_1$, $\omega_2$, $\zeta_1$, and $\zeta_2$ are chosen as $\omega_1=2\pi/t_p$, $\zeta_1=0.95$, $\omega_2=1.82\ \omega_1$, $\zeta_2=0.8$, and $t_p$ represents a dispersive unit of delay.

6. The system of claim 1, wherein the filtering means includes a computerized predictor.

7. The system of claim 6, wherein the computerized predictor is a Kalman filter.

8. The system of claim 6, wherein the computerized predictor is a linear extrapolator.

9. A system for utilizing bolus propagation for contrast enhancement in CT angiography comprising:
   (a) an output device for injecting a bolus into a biological structure having a plurality of organs and vessels and being positioned on a table;
   (b) a scanner for generating CT fluoroscopy image data of the bolus along a path in the biological structure; and
   (c) a processor for performing the steps of:
      (i) determining a predicted position of the bolus using a bolus propagation model with a set of parameters prior to the arrival of the bolus at a location of the path by performing the substeps of:
         (1) Defining an extended vascular operator for each of the plurality of organs and vessels with three parameters T, D and L, where T is the time counting from the bolus injection, D is the dispersion and L is the length of the path;

(2) Selecting a plurality of locations $p_i$ along the path, i=0, 1, ..., N, N is an integer greater than one, where real-time measurements can be made on each location $p_i$ by the monitoring means;

(3) Selecting a time threshold value $\epsilon$ and a dispersion threshold value $\delta$;

(4) Defining a velocity variable $A_i$ and a relative dispersion variable $B_i$ for each of the plurality of locations $p_i$ along the path, where i=i+1;

(5) Setting $A_i=A_{i-1}$ and $B_i=B_{i-1}$, wherein $A_0=L/T$ and $B_0=D/T$;

(6) Predicting the peak arrival time $t(p_i)$ and the relative dispersion $B(p_i)$ of the bolus at the location $p_i$ according to the following:

$$t(p_i)=t(p_{i-1})+(p_i-p_{i-1})/A_i,$$

and $$B(p_i)=B_i;$$

(7) Measuring the peak arrival time $t'(p_i)$ and the relative dispersion $B'(p_i)$ of the bolus at the location $p_i$;

(8) If $|t'(p_i)-t(p_i)|>\epsilon$, updating the velocity variable $A_i$ according to the following formula:

$$A_i=(p_i-p_{i-1})/(t'_i-t'_{i-1});$$

(9) If $|B'(p_i)-B(p_i)|>\delta$, updating the relative dispersion $B(p_i)$ of the bolus according to the following formula:

$$B_i=B'(p_i);$$

(10) Updating T and D according to the following:

$$T=t_i+(L-p_i)/A_i;$$

and $$D=B_i;$$

and

(11) repeating steps (6)–(10) until all points of interest in the plurality of locations $p_i$ along the path have been selected and the predicted position of the bolus is determined; and (ii) comparing the predicted position of the bolus with the image data of the bolus;

(d) a computerized predictor for reconciling discrepancy, if any, between the predicted position of the bolus and the image data of the bolus to extrapolate a set of control parameters; and (e) a table transport system for adaptively transporting the table to chase the motion of the bolus according to the set of control parameters.

10. The system of claim 9, wherein the extended vascular operator represents the bolus concentration as a function of the variables t, p and L, wherein t=T and p is the point of interest at time t.

11. The system of claim 10, wherein the extended vascular operator takes the following form:

$$C(p, t)=h(p, t)\otimes C_{in}(t),$$

where C(p, t) is the extended vascular operator, $$h(p, t)=(L/p)H((L/p)t),$$

$$H(t)=f_0(t)\otimes f_1(t)\otimes f_2(t),$$

$$f_0(t)=\delta(t-t_d),$$

$$f_1(t)=\exp(-\zeta_1\omega_1 t)\cos(\omega_1(1-\zeta_1^2 t)^{1/2}+\theta_1)u(t)/(1-\zeta_1^2)^{1/2},$$

$$\theta_1=-\cos^{-1}((1-\zeta_1^2)^{1/2})-\pi,$$

$$f_2(t)=\exp(-\zeta_2\omega_2 t)\cos(\omega_2(1-\zeta_2^2 t)^{1/2}+\theta_2)u(t)/(1-\zeta_2^2)^{1/2},$$

and $$\theta_2=-\cos^{-1}((1-\zeta_2^2)^{1/2})-\pi,$$

with $\omega_1$, $\omega_2$ being the natural frequency, $\zeta_1$, $\zeta_2$ being the damping factor, and $t_d$ representing a transmission line of delay.

12. The system of claim 11, wherein $\omega_1$, $\omega_2$, $\zeta_1$, and $\zeta_2$ are chosen as $\omega_1=2\pi/t_p$, $\zeta_1=0.95$, $\omega_2=1.82\ \omega_1$, $\zeta_2=0.8$, and $t_p$ represents a dispersive unit of delay.

13. The system of claim 9, wherein the computerized predictor is a Kalman filter.

14. The system of claim 9, wherein the computerized predictor is a linear extrapolator.

15. A computer-readable, digital storage device storing executable instructions which cause a processor to utilize bolus propagation for contrast enhancement in a biological structure having a plurality of organs and vessels and being positioned on a table by:

(a) receiving image data associated with a bolus moving along a path in the biological structure;

(b) determining a predicted position of the bolus using a bolus propagation model with a set of parameters prior to the arrival of the bolus at a location of the path;

(c) comparing the predicted position of the bolus with the image data associated with the bolus to update the parameters;

(d) reconciling discrepancy, if any, between the predicted position of the bolus and the image data of the bolus to extrapolate a set of control parameters; and (e) feeding the set of control parameters to a control unit for adaptively transporting the table to chase the motion of the bolus accordingly.

16. The device of claim 15, wherein the predicted position of the bolus is determined by performing the substeps of:

(1) Defining an extended vascular operator for each of the plurality of organs and vessels with three parameters T, D and L, where T is the time counting from the bolus injection, D is the dispersion and L is the length of the path;

(2) Selecting a plurality of locations $p_i$ along the path, i=0, 1, ..., N, N is an integer greater than one, where real-time measurements can be made on each location $p_i$ by the monitoring means;

(3) Selecting a time threshold value $\epsilon$ and a dispersion threshold value $\delta$;

(4) Defining a velocity variable $A_i$ and a relative dispersion variable $B_i$ for each of the plurality of locations $p_i$ along the path, where i=i+1;

(5) Setting $A_i=A_{i-1}$ and $B_i=B_{i-1}$, wherein $A_0=L/T$, and $B_0=D/T$;

(6) Predicting the peak arrival time $t(p_i)$ and the relative dispersion $B(p_i)$ of the bolus at the location $p_i$ according to the following:

$$t(p_i)=t(p_{i-1})+(p_i-p_{i-1})/A_2,$$

and $$B(p_i)=B_i;$$

(7) Measuring the peak arrival time $t'(p_i)$ and the relative dispersion $B'(p_i)$ of the bolus at the location $p_i$;

(8) If $|t'(p_i)-t(p_i)|>\epsilon$, updating the velocity variable $A_i$ according to the following formula:

$$A_i=(p_i-p_{i-1})/(t'_i-t'_{i-1});$$

(9) If $|B'(p_i)-B(p_i)|>\delta$, updating the relative dispersion $B(p_i)$ of the bolus according to the following formula:

$$B_i=B'(p_i);$$

(10) Updating T and D according to the following:

$$T=t_i+(L-p_i)/A_i;$$

and $$D=B_i;$$

and

(11) repeating steps (6)–(10) until all points of interest in the plurality of locations $p_i$ along the path have been selected.

17. The device of claim 16, wherein the extended vascular operator represents the bolus concentration as a function of the variables t, p and L, wherein t=T and p is the point of interest at time t.

18. The device of claim 17, wherein the extended vascular operator takes the following form:

$$C(p, t)=h(p, t)\otimes C_{in}(t),$$

where C(p, t) is the extended vascular operator, $$h(p, t)=(L/p)H((L/p)t),$$

$$H(t)=f_0(t)\otimes f_1(t)\otimes f_2(t),$$

$$f_0(t)=\delta(t-t_d),$$

$$f_1(t)=\exp(-\zeta_1\omega_1 t)\cos(\omega_1(1-\zeta_1^2 t)^{1/2}+\theta_1)u(t)/(1-\zeta_1^2)^{1/2},$$

$$\theta_1=-\cos^{-1}((1-\zeta_1^2)^{1/2})-\pi,$$

$$f_2(t)=\exp(-\zeta_2\omega_2 t)\cos(\omega_2(1-\zeta_2^2 t)^{1/2}+\theta_2)u(t)/(1-\zeta_2^2)^{1/2},$$

and $$\theta_2=-\cos^{-1}((1-\zeta_2^2)^{1/2})-\pi,$$

with $\omega_1$, $\omega_2$ being the natural frequency, $\zeta_1$, $\zeta_2$ being the damping factor, and $t_d$ representing a transmission line of delay.

19. The device of claim 13, wherein $\omega_1$, $\omega_2$, $\zeta_1$, and $\zeta_2$ are chosen as $\omega_1=2\pi/t_p$, $\zeta_1=0.95$, $\omega_2=1.82\ \omega_1$, $\zeta_2=0.8$, $t_p$ represents a dispersive unit of delay.

20. A method for utilizing bolus propagation for contrast enhancement in CT angiography comprising the steps of:

(a) monitoring the position of a bolus moving along a path in a biological structure, wherein the biological structure has a plurality of organs and vessels and is positioned on a table;

(b) determining a predicted position of the bolus using a bolus propagation model with a set of parameters prior to the arrival of the bolus at a location of the path;

(c) comparing the predicted position of the bolus with the measured position of the bolus;

(f) reconciling discrepancy, if any, between the predicted position of the bolus and the image data of the bolus to a set of control parameters; and (g) transporting the table to chase the motion of the bolus according to the set of control parameters.

21. The method of claim 20, wherein the step of determining a predicted position of the bolus comprises the substeps of:

(1) Defining an extended vascular operator for each of the plurality of organs and vessels with three parameters T, D and L, where T is the time counting from the bolus injection, D is the dispersion and L is the length of the path;

(2) Selecting a plurality of locations $p_i$ along the path, i=0, 1, ..., N, N is an integer greater than one, where real-time measurements can be made on each location $p_i$ by the monitoring means;

(3) Selecting a time threshold value $\epsilon$ and a dispersion threshold value $\delta$;

(4) Defining a velocity variable $A_i$ and a relative dispersion variable $B_i$ for each of the plurality of locations $p_i$ along the path, where i=i+1;

(5) Setting $A_i=A_{i-1}$ and $B_i=B_{i-1}$, wherein $A_0=L/T$, and $B_0=D/T$;

(6) Predicting the peak arrival time $t(p_i)$ and the relative dispersion $B(p_i)$ of the bolus at the location $p_i$ according to the following:

$$t(p_i)=t(p_{i-})+(p_i-p_{i-1})/A_i,$$

and $$B(p)=B_i;$$

(7) Measuring the peak arrival time $t'(p_i)$ and the relative dispersion $B'(p_i)$ of the bolus at the location $p_i$;

(8) If $|t'(p_i)-t(p_i)|>\epsilon$, updating the velocity variable $A_i$ according to the following formula:

$$A_i=(p_i-p_{i-1})/(t'_i-t'_{i-1});$$

(9) If $|B'(p_i)-B(p_i)|>\delta$, updating the relative dispersion $B(p_i)$ of the bolus according to the following formula:

$$B_i=B'(p_i);$$

(10) Updating T and D according to the following:

$$T=t_i+(L-p_i)/A_i;$$

and $$D=B_i;$$

and

(11) repeating steps (6)–(10) until all points of interest in the plurality of locations $p_i$ along the path have been selected.

22. The method of claim 21, wherein the extended vascular operator represents the bolus concentration as a function of the variables t, p and L, wherein t=T and p is the point of interest at time t.

23. The method of claim 22, wherein the extended vascular operator takes the following form:

$C(p, t) = h(p, t) \otimes C_{in}(t),$ where C(p, t) is the extended vascular operator, $h(p, t) = (L/p)H((L/p)t),$ $H(t) = f_0(t) \otimes f_1(t) \otimes f_2(t),$ $f_0(t) = (t - t_d),$ $f_1(t) = \exp(-\zeta_1\omega_1 t)\cos(\omega_1(1-\zeta_1^2 t)^{1/2} + \theta_1)u(t)/(1-\zeta_1^2)^{1/2},$ $\theta_1 = -\cos^{-1}((1-\zeta_1^2)^{1/2}) - \pi,$ $f_2(t) = \exp(-\zeta_2\omega_2 t)\cos(\omega_2(1-\zeta_2^2 t)^{1/2} + \theta_2)u(t)/(1-\zeta_2^2)^{1/2},$ and $\theta_2 = -\cos^{-1}((1-\zeta_2^2)^{1/2}) - \pi,$ with $\omega_1$, $\omega_2$ being the natural frequency, $\zeta_1$, $\zeta_2$ being the damping factor, and $t_d$ representing a transmission line of delay.

24. The method of claim 23, wherein $\omega_1$, $\omega_2$, $\zeta_1$ and $\zeta_2$ are chosen as $\omega_1 = 2\pi/t_p$, $\zeta_1 = 0.95$, $\omega_2 = 1.82\ \omega_1$, $\zeta_2 = 0.8$, and $t_p$ represents a dispersive unit of delay.

* * * * *